United States Patent [19]
Kesling

[11] Patent Number: 4,781,582
[45] Date of Patent: Nov. 1, 1988

[54] CONVERTIBLE BUCCAL TUBE ASSEMBLY
[75] Inventor: Peter C. Kesling, LaPorte, Ind.
[73] Assignee: TP Orthodontics, Inc., Westville, Ind.
[21] Appl. No.: 43,038
[22] Filed: Apr. 27, 1987
[51] Int. Cl.$^4$ .............................................. A61C 3/00
[52] U.S. Cl. .................................................... 433/17
[58] Field of Search ......................... 433/17, 8, 16, 18
[56] References Cited
U.S. PATENT DOCUMENTS

| | | | |
|---|---|---|---|
| 3,218,715 | 11/1965 | Wallshein | 433/8 |
| 3,494,034 | 2/1970 | Kesling | 433/17 |
| 3,526,961 | 9/1970 | Kesling | 433/17 |
| 3,874,080 | 4/1975 | Wallshein | 433/17 |
| 4,028,809 | 6/1977 | Wallshein | 433/17 |
| 4,498,867 | 2/1985 | Kesling | 433/17 |

Primary Examiner—Gene Mancene
Assistant Examiner—Adriene J. Lepiane
Attorney, Agent, or Firm—Lloyd L. Zickert

[57] ABSTRACT

A convertible buccal tube assembly for selectively receiving archwire in non-torquing or torquing modes, which includes a buccal tube portion having a round archwire opening therethrough capable of receiving round or non-round archwire and a torquing flap with a rectangular or other non-round opening selectively positionable between non-working and working positions and movable into the working position with the rectangular opening aligning with the round opening of the buccal tube portion to convert the assembly for receiving a rectangular archwire in a torquing mode.

12 Claims, 1 Drawing Sheet

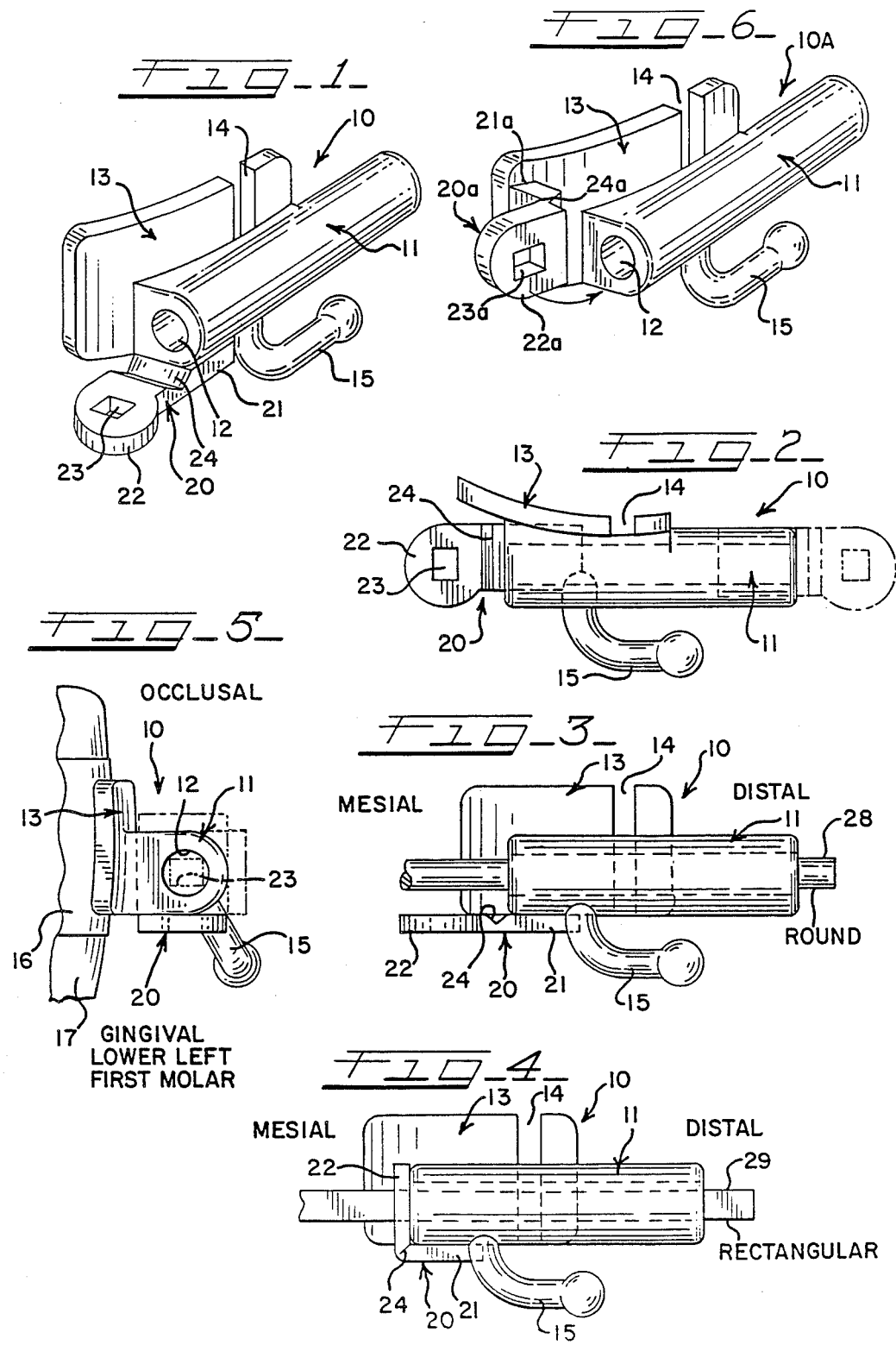

CONVERTIBLE BUCCAL TUBE ASSEMBLY

DESCRIPTION

This invention relates in general to a buccal tube assembly, and more particularly to a buccal tube assembly that is convertible for selectively receiving archwire in either a non-torquing or a torquing mode, and still more particularly to a buccal tube assembly for coacting with round or rectangular archwire in a non-torquing mode or with rectangular wire in a torquing mode.

BACKGROUND OF THE INVENTION

Orthodontic systems typically use round archwire connected to brackets and anchored in buccal tubes on molars or non-round archwires generally of rectangular cross section connected to brackets and anchored in buccal tubes. Round wire is generally used in the Begg technique, and rectangular wire is generally used in the edgewise technique. When round wire is used, it is not used for torquing, while rectangular wire can be used for applying torquing forces.

At some stage in the edgewise technique, it is advantageous to use round wire with edgewise brackets for accomplishing certain movements not concerned with torquing; thereafter, it is advantageous to use rectangular archwire where torquing is needed to accomplish certain teeth movement. Where round archwire is first used in an edgewise system, it would require the use of a buccal tube having a round opening, and when it is then desired to apply torquing forces, it is necessary to use a buccal tube having a rectangular opening. One method of handling both wires is to first mount round buccal tubes on the molars, and thereafter replace them with rectangular buccal tubes which requires considerable time of the orthodontist in the changeover process. More often, a double tube appliance having both round and rectangular tubes on the one base is used to avoid the need for a changeover. Such an appliance is bulky, and depending upon the arrangement of the tubes, they may protrude into the check or into the gingiva. Further, such an appliance may be subject to damaging occlusion forces and always requires archwire bending which is intended to be avoided by the straight wire technique.

It has been known to use buccal tube assemblies that are capable of accommodating round wire or doubled back wire forms, such as in U.S. Pat. No. 3,526,961. This patent predates the development of techniques used today where both round and rectangular wires are used over the complete treatment of a patient. There is now a need for facilitating the changing from round archwire use to rectangular archwire use.

SUMMARY OF THE INVENTION

The present invention solves a problem that exists with modern day techniques of orthodontia where it is desired over the period of treatment of a patient with edgewise appliances to use both round and rectangular archwire so that with a single molar-mounted buccal tube, the distal ends of an archwire can be selectively anchored at the same level in a non-torquing mode or in a torquing mode. This is accomplished by providing a buccal tube assembly with a single tube that is convertible for use with round archwire or rectangular archwire, thereby eliminating the necessity of changing tubes or using a double tube appliance.

The assembly of the present invention includes the standard buccal tube with a round opening that is capable of receiving either round or non-round archwire and which also includes one or more torquing flaps each in the form of a tab selectively positionable to be in non-working or working positions. In the non-working position the tab has no working relationship with the round opening of the buccal tube whereby it may receive round or non-round archwire in a non-torquing mode. In the working position the torquing flap changes the ultimate cross section of the buccal tube to a non-round configuration such as a rectangular configuration so that the buccal tube then coacts with a non-round archwire in a torquing mode. The torquing flap may be mounted on any side of the buccal tube or on the base for the tube, and thereafter is bendable into working position when desired.

It is therefore an object of the present invention to provide a new and improved buccal tube assembly that is convertible to receive round archwire in a non-torquing mode and to receive non-round archwire in a torquing mode where both wires may be received at the same level, thereby eliminating any bending of the wire.

Another object of the present invention is in the provision of a buccal tube assembly that is convertible to coact with either a round archwire in a non-torquing mode or a rectangular archwire in a torquing mode so that torquing forces can be applied between the archwire and the buccal tube.

A further object of the present invention is in the provision of a convertible buccal tube assembly including a buccal tube having a round opening and a torquing flap with a rectangular opening and bendable to align with the round opening to convert the buccal tube for applying torquing forces.

Other objects, features and advantages of the invention will be apparent from the following detailed disclosure, taken in conjunction with the accompanying sheets of drawings, wherein like reference numerals refer to like parts.

BRIEF DESCRIPTION OF THE DRAWINGS

FIG. 1 is a perspective view of the buccal tube assembly according to the present invention and showing the torquing flap in a non-working position;

FIG. 2 is a top plan view of the buccal tube assembly of FIG. 1;

FIG. 3 is a front or buccal view of the assembly of FIGS. 1 and 2 and also illustrating the tube as receiving a round archwire and where the torquing flap is in its non-working position;

FIG. 4 is a front or buccal view of the assembly similar to FIG. 3 but illustrating the torquing flap in its working position and the tube as receiving the rectangular archwire whereby torquing forces can be applied between the archwire and the buccal tube;

FIG. 5 is a mesial end view of the buccal tube assembly of the invention mounted on a lower left molar and also illustrating in broken lines alternate positions for the torquing flap; and FIG. 6 is a perspective view of a modified buccal tube assembly according to the invention where the torquing flap is mounted on the base of the appliance.

DESCRIPTION OF THE INVENTION

Referring now to the drawings, and particularly to FIG. 1, the buccal tube assembly of the present invention is generally indicated by the numeral 10 and includes a buccal tube 11 of the usual construction having a round opening 12 therethrough. The tube 11 is integral with or otherwise attached to a base or welding flange 13 that may be in turn suitably welded or otherwise secured to a bonding base or a band. A vertical slot 14 is provided in the welding flange 13 at a suitable location behind the buccal tube 11 and which may optionally serve to receive a pin, a tail of a spring, or any other auxiliary. Extending from and mounted from the buccal tube 11 is a ball-ended hook 15 that may optionally anchor a suitable elastic or other element. The assembly is illustrated in mounting relation on a band 16 that is cemented to a lower left molar tooth 17 in FIG. 5. Preferably, the assembly is welded to the band, but it may be attached by soldering. Further, the assembly may be secured to a bonding pad that is directly bonded to a tooth, or mesh may be attached to the base for bonding the appliance to a tooth. While the tube and base are shown to be integral and therefore may be cast in one piece, they may be separately formed and suitably secured together.

A torquing flap 20 is suitably attached to the gingival side of the buccal tube 11 and projects mesially. This flap includes a base 21 that may be suitably welded, soldered or otherwise secured to the buccal tube, a head 22 having a rectangular opening 23 therethrough, and a weakened or scored portion between the head and the base defining a hinge 24. Scoring of the torquing flap at the hinge 24 facilitates the ease of bending the head of the torquing flap into proper working position.

It will be appreciated that the torquing flap 20, while illustrated as mounted on the gingival side of the buccal tube, may be mounted on the occlusal, buccal or lingual side of the tube, as illustrated in broken lines in FIG. 5. Further, it could be configured for mounting directly on the base 13 of the appliance and bendable into coacting relation with the tube 11. When mounted on the lingual side of the tube, it will be mounted between the tube and the welding flange. Further, while the torquing flap is illustrated as being mounted on the mesial end of the buccal tube, it will be appreciated that it could be mounted on the distal end of the buccal tube. If desired, a torquing flap may be mounted at both ends of the tube, as shown in broken lines in FIG. 2. The rectangular opening 24 may be of any non-round shape, and it may be square with the buccal tube position, as shown in FIG. 5, or rotated at any desired position.

The torquing flap 20 is shown in its non-working or non-torquing position in FIGS. 1, 2, 3 and 5, and in its working or torquing position in FIG. 4. Normally, in the treatment of a patient, round archwire will be employed in the earlier stage or stages where it is not desired in induce any torquing forces, and accordingly, the present invention would be utilized with the torquing flap in a non-working position, as shown in FIGS. 1, 2, 3 and 5, so that it does not interfere with the operation of the round archwire. It also may be possible to use the assembly of the invention with the torquing flap in a non-working position where rectangular archwire is received by the round opening of the buccal tube. Thereafter, when it is desired to apply torque between the archwire and the buccal tube, the head of the torquing flap would be bent so that the rectangular opening 23 would align with the round opening 12 as illustrated in FIG. 5, whereby the tube would be converted for coacting with a rectangular wire and applying a torquing force.

FIG. 3 further illustrates the coaction of round archwire 28 with the buccal tube assembly and where the torquing flap is in non-working position. Similarly, with the torquing flap in working position, a rectangular archwire 29 is shown with the buccal tube assembly, as seen in FIG. 4.

The appliance embodiment 10A in FIG. 6 differs principally from the embodiment of FIG. 1 in that the torquing flap is mounted on the base 13 of the appliance. Here, the torquing flap 20a is generally Z-shaped ans suitably secured by its base 21a to the appliance base or welding flange 13. The head 22a is connected to the base 21a by a hinge 24a, whereby the head may be bent so that the rectangular opening 23a is aligned with the round opening 12 of the tube 11 and thereafter receive a rectangular archwire in a torquing mode.

It will therefore be appreciated that the present invention eliminates the need to change buccal tubes or to use a double tube appliance when it is desired to advance between stages and advance from using round archwire to rectangular archwire and for advancing to the point of using a non-round archwire for purposes of applying a torquing force between the archwire and the buccal tube. The torquing flap is simply mechanically bent into place when torquing is desired.

It will be understood that modifications and variations may be effected without departing from the scope of the novel concepts of the present invention, but it is understood that this application is to be limited only by the scope of the appended claims.

The invention is hereby claimed as follows:

1. A buccal tube assembly including a base, a tube having a round opening, and at least one torquing flap having a non-round opening and attached to said tube, said flap being mounted to normally extend substantially parallel to said tube and being bendable to align the non-round opening with the round opening thereby converting the assembly to receive a torquing force from a non-round archwire.

2. The assembly of claim 1, wherein said flap is mounted on the occlusal side of the tube.

3. The assembly of claim 1, wherein said flap is mounted on the gingival side of the tube.

4. The assembly of claim 1, wherein said flap is mounted on the buccal side of the tube.

5. The assembly of claim 1, wherein said flap is mounted on the lingual side of the tube.

6. The assembly of claim 1, wherein said flap is scored to facilitate bending into an operating position.

7. The assembly of claim 1, wherein said non-round opening is rectangular in shape.

8. The assembly of claim 1, wherein said flap is attached to the tube by welding.

9. The assembly of claim 1, wherein said flap is scored to facilitate bending of same into a position so that said opening in the flap aligns with said opening in said tube, and said flap opening being rectangular in shape to coact with rectangular in cross section archwire.

10. A buccal tube assembly including a base, a tube mounted on the base and having a round opening, and at least one torquing flap having a non-round opening and attached to said tube or base, said flap being mounted to normally extend substantially parallel to said tube and being bendable to align the non-round opening with the round opening thereby converting the assembly to receive a torquing force from a non-round archwire.

11. The assembly of claim 10, wherein said flap is mounted on the base.

12. In combination with an archwire, a buccal tube asembly including a tube having a round opening capable of receiving round or non-round archwire, and a torquing flap having a non-round opening and attached to said tube, said flap normally positioned to permit the tube to receive either round or non-round archwire in a non-torquing relation and being bendable to align said non-round opening with said round opening and convert the tube for receiving non-round archwire in a torquing relation.

* * * * *